United States Patent [19]

Marker

[11] Patent Number: 5,362,377
[45] Date of Patent: * Nov. 8, 1994

[54] CONVERSION OF OLEFINS BY CATALYTIC DISTILLATION

[75] Inventor: Terry L. Marker, Warrenville, Ill.

[73] Assignee: UPO, Des Plaines, Ill.

[*] Notice: The portion of the term of this patent subsequent to Sep. 7, 2010 has been disclaimed.

[21] Appl. No.: 120,095

[22] Filed: Sep. 13, 1993

Related U.S. Application Data

[62] Division of Ser. No. 902,179, Jun. 22, 1992, Pat. No. 5,258,560.

[51] Int. Cl.$^5$ .............. C10G 35/00; C07C 2/64; C07C 2/56; C07C 41/05
[52] U.S. Cl. ................ 208/133; 585/450; 585/719; 568/697; 203/DIG. 6
[58] Field of Search ............ 585/450, 468, 446, 467, 585/709, 719; 568/697; 502/81; 208/133; 203/DIG. 6

[56] References Cited

U.S. PATENT DOCUMENTS

| | | | |
|---|---|---|---|
| 3,506,408 | 4/1970 | Kageyama et al. | 23/288 |
| 3,634,535 | 1/1972 | Haunschild | 260/677 A |
| 3,821,123 | 6/1974 | Germanas et al. | 252/439 |
| 4,849,569 | 7/1989 | Smith, Jr. | 585/446 |
| 4,950,803 | 8/1990 | Smith, Jr. et al. | 568/697 |
| 5,215,725 | 6/1993 | Sy | 422/212 |
| 5,243,102 | 9/1993 | Marker et al. | 568/697 |

*Primary Examiner*—Asok Pal
*Assistant Examiner*—Bekir L. Yildirim
*Attorney, Agent, or Firm*—Thomas K. McBride; John F. Spears, Jr.

[57] ABSTRACT

Ethers suitable for use as high octane oxygenate additives for motor fuels are produced by a catalytic distillation process wherein a mixture of C$_4$-plus isoolefin(s) and an alcohol are recovered from a catalytic distillation zone as an overhead stream and charged to a packed liquid-phase reaction zone containing an etherification catalyst before being recycled to one or more portions of the overall catalytic distillation zone. The process is useful in the coprocessing of a mixture of isobutylene and isoamylene and in other hydrocarbon conversion processes such as hydration and alkylation.

5 Claims, 1 Drawing Sheet

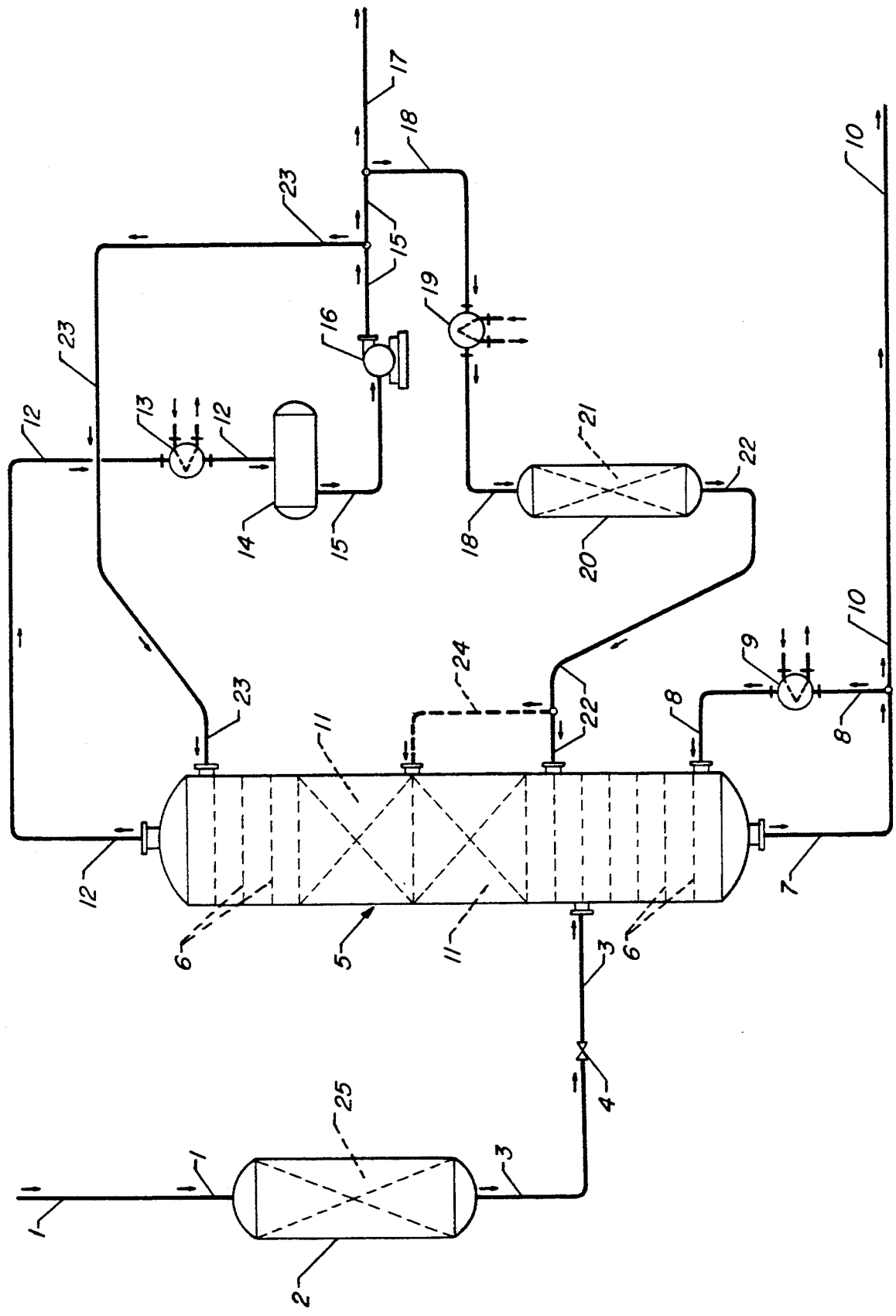

CONVERSION OF OLEFINS BY CATALYTIC DISTILLATION

CROSS-REFERENCE TO RELATED APPLICATIONS

This application is a division of my prior copending application Ser. No. 07/902,179 filed Jun. 22, 1992, now U.S. Pat. No. 5,258,560, with the entire teaching of my prior application being expressly incorporated herein.

FIELD OF THE INVENTION

The invention relates to a hydrocarbon conversion process useful in the etherification of isoolefins such as isobutylene. The process is especially useful in processing mixtures of isoolefins including isoamylenes or heavier $C_6$-plus tertiary olefins. The invention also relates to the use of catalytic distillation to perform hydrocarbon conversion reactions. The invention also specifically relates to a process wherein isohexylene is reacted with methanol or higher alcohols to form an ether.

PRIOR ART

U.S. Pat. No. 3,506,408 to O. Kageyama et al. illustrates the use of catalytic distillation for carrying out reversible liquid phase reactions such as the production of acetals and esters by the reaction of two organic feed compounds. This reference teaches the use of ion exchange resin particles located on shelves with layers of packing such as Raschig rings located above the catalyst.

U.S. Pat. No. 3,634,535 to W. Haunschild and the references incorporated therein are pertinent for showing that ethers including methyl tertiary butyl ether (MTBE) can be produced by catalytic distillation performed on distillation trays or with catalyst in the form of packing. Etherification by catalytic distillation using similar methods is also described in U.S. Pat. No. 4,950,803 issued to L. A. Smith et al.

The alkylation of aromatic hydrocarbons by catalytic distillation is described in U.S. Pat. No. 4,849,569 to L. A. Smith.

Catalysts and processes for the double bond isomerization of linear olefins are known in the art. For instance, U.S. Pat. No. 3,821,123 issued to D. Germanas et al. teaches the use of a sulfided nickel catalyst for this purpose.

BRIEF SUMMARY OF THE INVENTION

The invention is a hydrocarbon conversion process for the production of ethers which provides an increased yield of higher molecular weight ethers in a conventionally sized catalytic distillation unit. The invention also achieves higher conversions when processing a mixture of olefins, such as isobutylene and isoamylene, than is provided by a conventional catalytic distillation zone. The subject process can be used in a variety of petrochemical applications including the production of diisopropyl ether and the hydration olefins.

One broad embodiment of the invention may be characterized as a process for the production of ethers which comprises the steps of passing a mixture of at least one $C_4$-plus isoolefin and an alcohol into a catalytic distillation zone containing a central catalytic distillation section including an etherification catalyst, with the catalytic distillation zone being operated under conditions which result in the reaction of the alcohol with tertiary olefins and the separation of compounds present in the zone into an overhead stream comprising unreacted $C_4$-plus isoolefins and alcohol and a net bottoms stream which comprises a product ether, passing at least a portion of the overhead stream downward through a liquid-phase adiabatic etherification zone and releasing the effluent of the adiabatic etherification zone into the catalytic distillation zone below the catalytic distillation section.

BRIEF DESCRIPTION OF THE DRAWING

The drawing is a simplified process flow diagram showing a catalytic distillation column 5, and a close coupled reaction zone 20 which discharges its effluent into the catalytic distillation column via lines 22, 24 or 24'.

DETAILED DESCRIPTION AND PREFERRED EMBODIMENTS

The continuous quest for more economical processes for the production of petrochemicals is driving the development of etherification and alkylation processes employing "catalytic distillation". In these processes the conversion catalyst is retained within a structure or container capable of promoting vapor-liquid contact and fractional distillation. The catalyst is present in an overall apparatus which resembles a fractionation column. This apparatus is provided with means to effect reflux and reboiling of the apparatus and normally has vapor-liquid contacting devices, e.g., fractionation trays in its upper and lower ends.

In the case of exothermic reactions such as alkylation, the heat released by the reaction is allowed to vaporize a portion of the reactants. This causes the more volatile reactants to pass upward through the overall apparatus while the less volatile product hydrocarbons flow downward in a liquid phase. This allows a facile method for separating the product from the reactants. This fractionation within the reaction zone aids in product recovery but more importantly also tends to drive the alkylation reaction to completion by removing the product and supplying fresh reactants. A very high degree of conversion can therefore be achieved by employing catalytic distillation in suitable processes including etherification. The previously cited references describe catalytic distillation in detail.

It was suggested in the past to apply catalytic distillation to a wide variety of processes such as butene isomerization (U.S. Pat. No. 2,403,672 to M.P. Matuzak); the hydrolysis of low molecular weight olefin oxides to produce mono-alkylene glycols (U.S. Pat. No. 2,839,588 to A.S. Parker); and the production of MTBE as described above. These early disclosures did not lead to commercialization. Catalytic distillation is only now emerging as a commercially viable hydrocarbon conversion and petrochemical processing tool.

Advantages attributed to the catalytic distillation concept, wherein reaction products are continuously separated from the reactants and removed from the reaction zone by fractional distillation performed concurrently with the reaction, include a decrease in the capital cost of the plant needed to perform the process, the ability to achieve a higher degree of conversion, and the ability to perform processes which formerly were performed only in a batch type operation on a continuous basis. These advantages result from performing the reaction in a separation zone capable of removing the reaction products from the reactants and catalyst. Hence it is only necessary to provide one primary vessel and the reaction is not limited by chemical equilibrium.

The preferred apparatus for retaining the catalyst in the catalytic distillation zones is described in detail in U.S. Pat. No. 5,073,236 to A. P. Gelbein which is incorporated herein by reference for its teaching as to the structure and usage of these catalyst packing systems. These devices provide a means to evenly distribute the catalyst and reactants uniformly within the desired locations in the overall vessel. The apparatus is also very effective at promoting vapor-liquid contacting and therefore fractional distillation of the product(s) from the reactants.

It has recently been recognized that ethers formed from higher olefins, used herein to refer to $C_5$-plus, especially $C_6$-plus olefins, have very good octane numbers and are excellent gasoline blending components. This is set out in European Patent Application 0451 989 A1.

The etherification of higher olefins occurs at a much slower rate than the etherification of low olefins such as isobutylene. This requires reactors used for the etherification of higher olefins to contain more catalyst. As a catalytic distillation zone should contain a large amount of open space for vapor and liquid flow to promote efficient distillation, the catalyst density in a catalytic distillation zone is much lower than a conventional "packed" bed of catalyst. The added structure required for catalytic distillation also increases the total cost per pound of installed catalyst. These effects combine to require quite large and expensive catalytic distillation reactors for etherifying $C_6$-plus olefins.

It is an objective of the subject invention to provide an improved process for the production of high molecular weight ethers by catalytic distillation. It is a further objective to reduce the size of the catalytic distillation process unit required for the etherification of heavy olefins such as $C_5$–$C_8$ olefins with isopropyl alcohol. It is also an objective of the invention to provide a higher overall conversion when processing mixtures of olefins such as $C_4$ and $C_5$ isoolefins.

These objectives are achieved by employing both catalytic distillation and substantially liquid-phase adiabatic downflow reaction zones within the same overall catalytic distillation zone. The liquid phase reaction zone is "close coupled" to the catalytic distillation zone and is part of a recycle loop returning light reactants and some products to the catalytic distillation zone. This allows the process to increase the rate of ether production from an equal amount of catalytic distillation zone packing and to reduce the height and cost of the required apparatus. The reactants are preferably returned below the catalyst for a mixed ($C_4$/$C_5$) etherification and for $C_6$ isoolefins but above the catalyst for the etherification of single olefins, e.g., $C_5$ or $C_4$ isoolefins. This preference is based on trade-offs of conversion and vessel size.

The "close coupled" nature of the two reaction zones is shown by a preference for a minimal pressure drop (e.g., less than 10 psia) between the exit of the close coupled reactor and the catalytic distillation zone. This pressure drop is set in part by the phase of the reactants and the point of entrance to the catalytic distillation zone. Preferably no flow control valve is located in the connecting line. The reactants charged to the top of the liquid-phase reaction zone are restrained only by the inherent pressure drop of the closely packed catalyst employed in this zone and associated conduits. The reactants, which are slightly pressurized by a pump in the overhead system, enter the upper end of the reactor at a pressure about 5 psig above that present in the catalytic distillation zone. The temperature at the inlet of the liquid phase reactor is therefore closely controlled to maintain substantially liquid phase conditions. The presence of light reactants can lead to some limited vaporization.

The etherification reaction is quite exothermic. The liquid-phase reactor is operated in a substantially adiabatic condition and therefore the reactants are heated as they pass downward through the reaction zone. This is employed beneficially in the subject process as the heat of reaction is useful in promoting the partial vaporization of the material flowing into the catalytic distillation zone and minimizes any disruption in the temperature profile of the catalytic distillation zone without requiring any external heat exchange.

The majority of the discussion herein is directed to the preferred embodiment of higher olefin etherification. However, as those skilled in the art will recognize the invention is not so limited. The process of the subject invention can be applied in general to any reaction which is amendable to catalytic distillation and which is plagued by a slow reaction rate or other causes of low conversion. The undesired slow reaction rate can be attributable to the rate of reaction itself or to another closely related factor such as a diffusional resistance which limits the rate of reaction. A prime example of this is the hydration of olefinic hydrocarbons which is believed to be controlled to a great extent by the low mutual solubilities of the hydrocarbon and water phases.

Referring now to the Drawing, a feedstream comprising an admixture of methanol and $C_6$ monoolefins including tertiary monoolefins enters the process through line 1. In this instance, this feedstream admixture passes through a conventional liquid phase (plug flow) reaction zone 2 containing one or more beds 25 of resin catalyst prior to entering the catalytic distillation zone. The use of this prereactor(s) is desirable in some instances but is not considered to be a part of the subject invention. This contacting of the catalyst with the reactants effects a conversion of a sizeable amount (possible 50 mole %) of the isohexene of the feedstream into the corresponding ether by reaction with the methanol. The effluent line 3 of this reaction zone therefore contains an admixture of the feed methanol, the various $C_6$ monoolefins and some ether product. This stream is depressured in valve 4 and then continues passage through line 3 into a catalytic distillation zone 5. This zone or tower is composed of a lower fractionation section containing a plurality of vapor-liquid contacting or fractionation trays 6, a central section comprising two beds 11 containing a resin-type catalyst retained in the preferred packing structure and an upper fractionation zone containing an additional plurality of fractionation trays 6.

The reactor effluent stream of line 3 is preferably passed onto one of the fractionation trays 6 but could be passed onto one or more fractionation trays of the overall catalytic distillation zone 5 or, if desired, fed into the column at other points including in contact with the packing material containing the catalyst 11. It is highly preferred that the streams of lines 3 and 22 are passed into the zone 5 at a point sufficiently below the central section to ensure that substantially none of the ether present in these streams enters the central section. The catalyst in the central section therefore cannot promote the breakdown of the ether. The fractional distillation activity which occurs within the catalytic distillation zone results in the concentration of the product ether into the liquid phase material which travels downward through the column-like zone and eventually is removed as the bottoms stream carried by line 7. The bottoms stream is divided into a first portion removed as a product or net bottoms stream through line 10 and a second portion which is passed via line 8 through the reboiler 9 to provide heat and vapor at the bottom of the column.

The lighter components of the multi-phase stream of lines 3 and 22 rise upward through the catalytic distillation column 5 and ascend into the intermediate zone of this apparatus containing the catalyst. While in contact with the catalyst, additional quantities of methanol and the tertiary hexene olefin react to form additional amounts of the tertiary hexylmethylether. Fractionation of the various compounds occurs within this packed catalyst retaining zone resulting in the product ether descending downward. The feed methanol and olefins continue to rise upward through the overall apparatus at the conditions which are preferred for its operation. The material exiting the top of the uppermost catalyst retaining zone will contain an admixture of all three basic components: the alcohol, olefin and product ether.

The fractionation trays or other fractional distillation material such as packing located in the top of the catalytic distillation column performs an additional separation as required to remove essentially all of the product ether from the vapor phase material which is withdrawn from the top of the zone 5 via line 12. The vapor phase material or net overhead vapor should therefore be essentially free of the product ether but will contain inert materials, such as $C_6$ paraffins, present in the feedstream which pass through the reaction zone and are not converted therein. These inert materials together with the methanol and remaining $C_6$ olefins are condensed in the overhead condenser 13 and collected as liquid phase material in the overhead receiver 14.

A stream of liquid phase overhead material is removed through line 15 and divided into a first portion returned to the upper end of the catalytic distillation zone 5 through line 23 as reflux. A second portion of the overhead liquid of line 15 is removed through line 17 as a net overhead product removed as a drag stream for the purpose of eliminating from the process any paraffinic hydrocarbons present in the feedstream of line 1.

A third portion of the overhead liquid is diverted through line 18 and warmed in a heat exchanger 19 to a desired etherification temperature. This stream, which is at a higher pressure than the fractional catalytic column 5 due to passage through the pump 16, is fed into an upper end of a packed plug flow liquid phase etherification reactor 20. This reactor contains a bed 21 of solid resin catalyst. The contacting of the methanol and olefinic hydrocarbons present in the overhead liquid with the catalyst results in an additional amount of the desired product tertiary hexylmethylether being formed. The effluent of the reactor 20 is removed via line 22 and passed directly into the catalytic distillation column 5. Preferably, this is done at a point below the catalyst beds 11 but as shown on the Drawing a portion or all of the effluent of the reactor 20 may be passed into the catalytic distillation column 5 at other points containing the etherification catalyst such as between the two catalyst beds shown in the apparatus or even above the catalyst retaining sections 11 via line 24'. In this manner, the unreacted feed components present in the overhead stream are exposed to a larger quantity of catalyst and are brought down to a lower point in the apparatus which allows their upward passage as vapor.

The subject invention is not limited to any particular catalyst composition or structure. The presently preferred catalysts are the previously referred to acidic resin catalysts, but other catalysts can be utilized in the process including zeolitic catalysts comprising beta zeolite or Y zeolite.

The etherification embodiment of the subject process consumes two different reactants. The first is one or more $C_5$–$C_8$ tertiary olefin such as an amylene ($C_5H_{10}$), hexylene ($C_6H_{12}$), heptylene or octylene ($C_8H_{16}$). It is contemplated that in the normal commercial application of the subject process these olefinic reactants, which are branched at the double bond, will be present in a mixture of other branched and straight chain olefinic hydrocarbons having the same number of carbon atoms per molecule. Therefore, a preferred feed olefin, such as isoamylene, will normally be present in the feed stream in admixture with one or more amylene isomers: 1. 1-pentene, (n-propylethylene), 2. 2-pentene, (sym-methylethylethylene), 3. 2-Me-1 butene, (unsym-methylethylethylene), 4. 2-Me-2-butene, (trimethyethylene), and 5. 3-Me-1-butene (isopropylethylene). The expected olefin feed streams to the subject process will be derived from a fluid catalytic cracking (FCC) reaction zone, a thermal cracker or similar large scale refining process and are expected to contain a mixture of all of the possible $C_5$ or $C_6$ or $C_7$, etc. isomers in an approximate equilibrium concentration. The olefin feed stream also can be derived from the effluent of a dehydrogenation process. The feed or effluent to this process may be fractionated to result in a product containing only molecules having the same number of carbon atoms. This olefin stream could be further purified as by adsorptive separation to yield a high purity olefin feed stream.

The second reactant consumed in the etherification embodiment of the process is a $C_1$–$C_4$ acyclic alcohol such as methanol, ethanol, isopropanol or isobutanol. The product hydrocarbon can therefore be one of a wide variety of $C_6$–$C_{12}$ ethers including tertiary amyl methyl ether(TAME), tertiaryamyl ethyl ether, tertiary-amyl propyl ether, tertiary-amyl n-butyl ether, tertiary hexyl methyl ether (THME) and methyl tertiary heptyl ether. The preferred reactants are an amylene and methanol or ethanol.

While some of the higher boiling ethers resulting from the reaction of these reactants may not be suitable for use in gasoline, they may be useful in diesel fuel, jet fuel or other fuels or as feed stocks in petrochemical processes or as end product petrochemicals having their own utility.

The subject process can be practiced with any suitable catalysts. This may be any heterogeneous catalyst which gives satisfactory performance in terms of conversion and selectivity for the desired reaction at the conditions required to allow fractional distillation of the reactants and products. The best catalysts to employ in the subject process will of course to a great extent depend upon the identity of the specific reactants to be converted in the process. It is contemplated that different catalysts could be employed in the catalytic distillation reaction zone and in the liquid-phase reaction zone.

The preferred etherification catalyst is a macroporous acid form sulfonic ion exchange resin such as the sulfonated styrene-divinylbenzene resin as described in U.S. Pat. No. 2,922,822 having a degree of crosslinking of from about 5 to 60%. Suitable resins are available commercially. Specialized resins have been described in the art including copolymers of sulfonyl fluorovinyl ether and fluorocarbons as described in U.S. Pat. Nos. 3,784,399 and 3,849,243 Another specially prepared resin consists of the $SiO_2$-modified cation exchangers described in U.S. Pat. No. 4,751,343. The macroporous structure of a suitable resin is described in detail in U.S. Pat. No. 5,012,031 as having a surface area of at least 400 $m^2/g$, a pore volume of 0.6–2.5 ml/g and a mean pore diameter of 40–1000 angstroms. A particularly suitable and preferred catalyst is sold under the designation Amberlyst 15 and Amberlyst 35 by Rohm & Haas.

It is contemplated that the subject process could be performed using a metal-containing resin which contains one or more metals from sub-groups VI, VII or VIII of the Periodic Table such as chromium, tungsten, palladium, nickel, chromium, platinum, or iron as described in U.S. Pat. No. 4,330,679.

Various etherification process techniques, reaction conditions and product recovery methods are described in U.S. Pat. Nos. 4,219,678 to Obenous et al. and 4,282,389 to Droste et al. which are incorporated herein for this teaching.

There are many possible variations to the process embodiment shown in the Drawing. For instance the feed streams of line 1 and 2 may be charged to the catalytic reaction zone separately and at other points than shown in the drawing and the primary reactor 2 deleted. An internal overhead condenser can be employed instead of an external condenser. Other possible variations relate to the construction of the vapor-liquid contacting and catalyst retention devices employed in the process. The Drawing illustrates the use of fractionation trays. These may be any suitable type of tray with a sieve tray having a conventional downcomer arrangement being suitable. Another suitable type of fractionation tray is referred to as a Multiple Downcomer tray. This type of tray is described in U.S. Pat. No. 3,410,540. Those portions of the overall vessel devoted to fractionation can alternatively contain structured or dumped packing material and suitable liquid distributors. These devices provide a means to evenly distribute the catalyst within the desired locations in the vessel and also are effective in promoting vapor-liquid contacting.

While a structured catalyst retention device resembling structured column packing is preferred, there are other methods of retaining catalyst within the column which should also prove effective. For instance it is known that the catalyst may be retained upon the surface of perforated or sieve trays by the use of screens or bags or other particle retention means. It is also known that catalyst may be retained within downcomers used to convey liquid between fractionation trays.

While it is preferred that catalyst is present only in the central catalyst retaining section the process may be practiced with other configurations including the distribution of catalyst along the height of the catalytic distillation zone or column.

Temperatures which are suitable for use in the subject process may be the same as those employed in a conventional etherification process. The combination of temperature and pressure must be selected to maintain only a portion of the compounds in the catalytic distillation zones present as liquids since the etherification reaction is a liquid phase reaction and vapor is needed for distillation. Vapor is desired only as necessary to effect distillation. Suitable temperatures are from about 30° to about 140° C., especially from about 50° to about 100° C. Pressures which are suitable for use herein preferably are above about 1 atmosphere but should not be in excess of about 130 atmospheres. An especially desirable pressure range is from about 1.2 to about 20 atmospheres. The concept of space velocity does not apply to catalytic distillation. The reactants should be fed to the vessel in the proper stoichiometric ratio at a rate equal to their rate of consumption therein, which is most easily measured by monitoring the rate of ether production.

The liquid phase reaction zone(s), which do not employ catalytic distillation, are preferably maintained at an inlet temperature of 40°–100° C. and a pressure sufficient to maintain at least most of the reactive olefins in liquid phase conditions. A pressure of from 1.2 to 30 atmospheres is preferred.

The operation of the subject invention may be illustrated by the following example which is based upon an engineering design and computer simulations. The feedstream of line 1 would contain approximately 344 moles per hour methanol and 633 moles per hour of a mixed paraffin/olefin $C_6$ stream. This feed admixture would be contacted with an initial bed 25 of resin-type catalyst present in a quantity of approximately 50 cubic meters and maintained at a pressure of 36 psia (248 kpa) at 58 degrees Centigrade. The effluent stream of this reaction zone would be depressured to approximately 26 psia (179 kpa) and passed into the fractional distillation zone. This column would contain about 30 sieve-type trays in the lower portion of the column and about 8 trays in the upper portion of the column. The stream of line 3 would enter eighteen trays below the structured catalyst packing 11. The preferred structural packing referred to above would be present in the intermediate portion of the column. This portion of the column would contain approximately 74 cubic meters of the catalyst-containing packing material. The catalytic distillation column 5 would be operated at conditions which include a temperature of approximately 68 degrees Centigrade and 23 psia (158 kpa), with these conditions being measured at a central location within the catalyst retention media 11. The overhead stream of line 12 would have a flow rate of approximately 137,840 kg per hour and would be cooled to a temperature of approximately 46 degrees Centigrade to effect its condensation. Approximately 51,690 kilogram per hour of this material would be passed to the upper portion of column 5 as reflux. A portion of the overhead liquid equal to about 20,676 kg per hour would be withdrawn as the dragstream or net overhead product with the remainder of this material being passed into the close coupled side reactor 20. The closed coupled side reactor would be operated at an inlet pressure of about 31 psia (213 kpa) and an inlet temperature of about 54 degrees Centigrade. The effluent of this close coupled reactor 20 is expected to have a temperature of approximately 60 degrees Centigrade and contain 2100 kg/hr of tertiary hexylmethylether. This effluent stream is returned to the catalytic distillation zone at a point near the feedpoint of line 3. The net overhead liquid stream of line 17 will have a concentration of approximately 14 wt. percent methanol, 37.0 wt. percent unreactive $C_6$ olefins and 37% paraffins. The overhead will also contain 4.5% reactive $C_6$ olefins and 5.4% cylcopentene. This net overhead stream may be passed to a waterwash column or other appropriate materials for the recovery of the methanol. The net bottoms stream of line 10 will contain approximately 7760 kilograms per hour of tertiary hexylmethylether.

The subject process provides a very notable improvement in the etherification of mixtures of two or more olefins of different carbon number. The table below gives the results of computer simulations of conventional catalytic distillation and close coupled catalytic distillation compared to a base case conventional once-through liquid phase reactor system. The results are based upon feeding a 50/50 mixture of isobutylene and isoamylene (plus associated $C_4$ and $C_5$'s) to reaction zones optimized for each type of reactor. The effluent of the once through reactor is used as the feed to the conventional catalytic distillation reactor and close coupled reactor system.

| Conversion (mole %) | (base case) Once through Liquid phase | (base plus) Catalytic distillation | (base plus) Close coupled catalytic distillation |
|---|---|---|---|
| isobutylene | 95.0 | 93.9 | 98.0 |
| isoamylene | 65 | 90 | 95 |

Notice that isobutylene conversion actually decreases in the reactive distillation unit because of decomposition of the MTBE to form isobutylene and methanol. This occurs because the close boiling points of $C_5$'s and MTBE make it impossible to increase isoamylene conversion to TAME without getting a slight decrease in isobutylene conversion. Therefore, increasing reactive distillation height will not increase conversion to both TAME and MTBE but only to TAME. To get high conversions to both, the closed coupled reactor catalytic distillation system is required.

As mentioned above, the subject process can be used to perform reactions other than etherification. These reactions include esterification and olefin hydration reactions. Of these two reactions, hydration to produce alcohols suitable for use in motor fuels is the most desirable. Further, as described in U.K. Patent Application 2 187 741 A, water may be added during etherification to coproduce an alcohol during etherification.

The hydration of olefinic hydrocarbons can be performed at known conditions using conventional acidic resin catalysts in a catalytic distillation column. Hydration conditions in general would include a temperature of from 40 to 150 degrees Centigrade, preferably 40 to 60 degrees Centigrade, and a pressure of from about 26 to 500 psig (180–3450 kpa). In general the hydration conditions would be quite similar to those employed in etherification. The hydration and etherification of olefins to produce motor fuel blending components is described in U.S. Pat. Nos. 4,886,918 and 4,935,552 and in European Patent Application 0451989A1 which are incorporated herein by reference for their teaching of suitable reaction conditions, feedstocks and operation.

One embodiment of the subject invention is therefore a process for the hydration of olefinic hydrocarbons to form a corresponding alcohol. Water would therefore be charged to the process as a feed compound. Examples of the alcohols which could be produced include tertiary butyl alcohol, tertiary amyl alcohol and tertiary hexyl alcohol. The process of the subject invention can also be employed in a process wherein both ethers and alcohols are produced or in a process for the sequential production of an alcohol followed by its conversion to an ether. It is therefore contemplated that diisopropylether could be produced by first hydrating propylene and then reacting the resultant isopropyl alcohol with additional propylene.

The subject hydrocarbon conversion process can also be applied to other additive type reactions such as alkylation. This includes the alkylation of paraffins including isobutane and the alkylation of aromatic hydrocarbons including benzene and toluene. The former reaction can be used to produce motor fuel while the latter can be used to produce ethyl benzene, isopropyl benzene, dialkylbenzenes or heavier $C_{15}$–$C_{30}$ linear alkylbenzenes suitable for use in detergent manufacture. The reactant added to these substrate hydrocarbons may be either a $C_2$–$C_{20}$ olefin or an olefin-acting compound such as a light alcohol, e.g., methanol or ethanol.

These alkylation reactions are preferably promoted by a solid acid catalyst. Examples of some acid materials which can be employed in these catalysts are amorphous silica-alumina, fluoride treated silica-alumina, fluoride treated alumina, acid resins, Y zeolites and dealuminated Y zeolites, ZSM-5 zeolites, beta zeolites, omega zeolite and silicalite. Suitable alkylation catalysts are described in U.S. Pat. Nos. 4,469,908; 4,489,214; 4,459,426 and 4,365,104 which are incorporated herein for their teaching as to catalyst formulation and reaction conditions.

Processes for alkylation via catalytic distillation have been described in the open literature including U.S. Pat. Nos. 4,935,577; 5,082,990; 5,019,669 and 4,849,569. These patents are incorporated herein for their teaching as to the performance of alkylation in a catalytic distillation reaction zone.

Alkylation zones employed in the subject process will be operated at conditions which preferably maintain at least a portion of the reactants and a majority of the product hydrocarbons present in a liquid phase while in contact with the catalyst. Alkylation reactions can be performed over an extremely wide range of conditions including a temperature of from about 0 to 200 degrees Centigrade, preferably from 20 to 150 degrees C., and a pressure of atmospheric to 500 psig, preferably from 20 to 200 psig (1380 kpa).

A broad embodiment of the subject invention may therefore be characterized as a hydrocarbon conversion process which comprises the steps passing a first reactant and a second reactant into a catalytic distillation zone comprising upper and lower fractionation sections and a central catalytic distillation section and maintained at mixed-phase conversion conditions which are effective to promote both the exothermic reaction of the first and second reactants and fractional distillation of the contents of the catalytic distillation zone into an overhead vapor stream comprising the first and second reactants and a bottoms stream which is rich in a product compound which is less volatile than either the first or the second reactants; condensing the overhead vapor stream to produce an overhead liquid, passing a first portion of the overhead liquid into the catalytic distillation zone as reflux and removing a second portion of the overhead liquid as a net overhead product; passing a third portion of the overhead liquid into an external reaction zone operated at liquid-phase conversion conditions and producing a reaction zone effluent stream, with the external reaction zone being operated in a manner which allows the heat of reaction of the ongoing reaction to heat the reactants present in the external reaction zone; passing an effluent stream removed from the external reaction zone into the catalytic distillation zone; and, removing at least a portion of the bottoms stream from the process as a product stream.

The subject conversion process can be used as a separate process unit or as part of an integrated complex. In such an integrated complex any hydrocarbons which are not reacted in the process, such as isobutane present in the feed stream used to produce MTBE, can be recycled to a dehydrogenation unit for the production of additional isobutylene.

While it is presently preferred that the different reactors contain the same catalyst, there is no absolute requirement for this. The close coupled reactor 20 and the prereactor(s) 2 may therefore contain a different catalyst than the catalytic distillation zone 5. For instance, the different reactant concentrations and somewhat different reaction zone operating conditions may make different catalysts more effective or selective in promoting the desired reaction. It is also contemplated that two or more catalysts having totally different functions could be employed within the process. For instance, the close coupled reaction zone or the catalytic distillation zone may contain an olefin skeletal or double bond isomerization catalyst in addition to the etherification catalyst. The catalysts could be present as a physical admixture or in separate layers or zones distributed in different regions of either reactor. The reaction zones may therefore comprise an admixture of a resin etherification catalyst and a zeolitic isomerization catalyst. One or both of the reaction zones may also contain a catalyst containing a nonzeolitic molecular sieve (NZMS) as described in U.S. Pat. Nos. 4,864,068 and 5,114,563.

What is claimed:

1. A hydrocarbon conversion process which comprises the steps:

(a) passing a first reactant and a second reactant into a catalytic distillation zone maintained at mixed-phase conversion conditions which are effective to promote both the exothermic reaction of the first and second reactants and fractional distillation of the contents of the catalytic distillation zone into an overhead vapor stream comprising the first and second reactants and a bottoms stream which is rich in a product compound which is less volatile than either the first or second reactants;

(b) condensing the overhead vapor stream to produce an overhead liquid, passing a first portion of the overhead liquid into the catalytic distillation zone as reflux and removing a second portion of the overhead liquid as a net overhead product;

(c) passing a third portion of the overhead liquid into an external reaction zone operated at substantially liquid-phase conversion conditions and producing a reaction zone effluent stream, with the external reaction zone being operated in a manner which allows the heat of reaction of the ongoing reaction to heat the reactants present in the external reaction zone;

(d) passing an effluent stream removed from the external reaction zone into the catalytic distillation zone; and, (e) removing at least a portion of the bottoms stream from the process as a product stream.

2. The process of claim 1 further characterized in that the first reactant is an olefinic hydrocarbon and the exothermic reaction is alkylation.

3. The process of claim 2 further characterized in that the second reactant is an aromatic hydrocarbon.

4. The process of claim 2 further characterized in that the second reactant is a paraffin.

5. The process of claim 1 wherein the first reactant is water and the second reactant is a hydrocarbon.

* * * * *

UNITED STATES PATENT AND TRADEMARK OFFICE
CERTIFICATE OF CORRECTION

PATENT NO. : 5,362,377
DATED : November 8, 1994
INVENTOR(S) : Terry L. Marker

It is certified that error appears in the above-identified patent and that said Letters Patent is hereby corrected as shown below:

On title page, item [73],
change the assignee from "UPO" to --UOP--.

Signed and Sealed this

Thirty-first Day of January, 1995

Attest:

Attesting Officer

BRUCE LEHMAN

Commissioner of Patents and Trademarks